United States Patent [19]

Axford et al.

[11] 4,252,897

[45] Feb. 24, 1981

[54] METHOD AND APPARATUS FOR BACTERIA TESTING

[76] Inventors: Herbert G. Axford, 5 Masters Rd., Willowdale, Ontario; Jacob P. Jacob, R.R. #4, Tottenham, Ontario, both of Canada

[21] Appl. No.: 946,598

[22] Filed: Sep. 28, 1978

[30] Foreign Application Priority Data

May 3, 1978 [CA] Canada ................................. 302513

[51] Int. Cl.³ .............................................. C12Q 1/04
[52] U.S. Cl. ........................................ 435/34; 435/33; 435/289; 435/291; 435/293
[58] Field of Search ................... 435/30, 292, 293, 34, 435/35, 36, 37, 38, 39, 40, 3, 4, 29, 287, 289, 291, 299, 300, 301; 422/63, 64, 67, 104

[56] References Cited

U.S. PATENT DOCUMENTS

| | | | |
|---|---|---|---|
| 2,956,931 | 10/1960 | Goldberg | 435/34 X |
| 3,536,449 | 10/1970 | Astle | 422/63 X |
| 3,772,154 | 11/1973 | Isenberg et al. | 435/30 |
| 3,912,596 | 10/1975 | Haque et al. | 435/34 X |
| 3,928,140 | 12/1975 | Wyatt et al. | 435/291 X |
| 3,935,075 | 1/1976 | Perry et al. | 435/30 X |
| 3,936,356 | 2/1976 | Janin | 435/34 |
| 4,118,280 | 10/1978 | Charles et al. | 435/34 |

*Primary Examiner*—Robert J. Warden
*Attorney, Agent, or Firm*—Sim & McBurney

[57] ABSTRACT

There is provided a method and apparatus for bacterial testing, in which a multiple-pin inoculation head picks up bacterial samples in a compartmentalized sample tray and transfers these to a compartmentalized culture plate for incubation. The culture plate contains a test media to which some bacteria are sensitive. An indicator material is also included, which changes color upon pH change due to bacterial growth. The result is a geometric pattern of color, which is entered into a computer storage. Additional culture plates are also inoculated in the same way, each containing a different test medium together with an indicator. After all plates have been incubated and data entered into the storage, a computer facility compares the pattern of sensitivity of the unknown bacteria with known sensitivity patterns of known bacteria to determine the most likely identification for each of the unknown bacterial samples.

22 Claims, 6 Drawing Figures

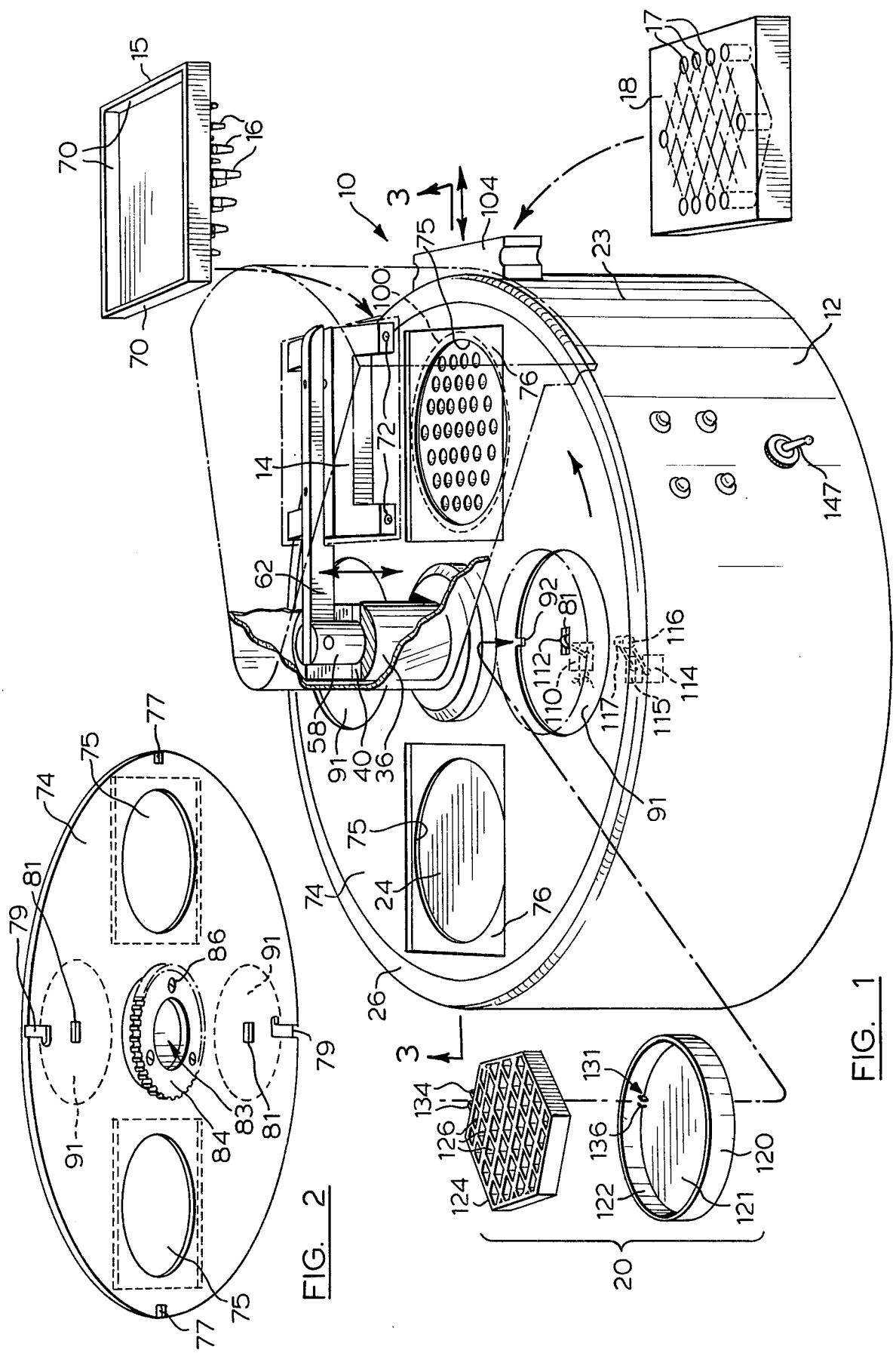

METHOD AND APPARATUS FOR BACTERIA TESTING

This invention relates generally to bacteriological identification procedures, and has to do particularly with a method and an apparatus for facilitating identification through the use of multiple inoculation techniques and computer-stored identification data.

BACKGROUND OF THIS INVENTION

Conventional microbiological laboratory techniques for the identification of a given bacterial sample are relatively complex and occupy considerable time on the part of the laboratory technician. The identification of a pathogenic strain on the throat swab of a patient presenting respiratory symptoms may be taken as an example. The technician must first culture the bacteria in the swab in order to produce enough of the bacterial sample to enable him to carry out the subsequent biochemical tests. Often, particularly in the case of swabs, there will be several bacteria present, not all of them pathogens. Various wellknown laboratory techniques are utilized to isolate and separate the different species one from the other. Generally speaking, each bacterial species can be distinguished from others by its particular reactions to certain known biochemicals. These may be sugars (dextrose, mannitol, lactose, etc.), amino acid preparations (lysine, ornithine, etc.), or preparations of specific substances such as urea, which certain bacteria can "use" for their growth, and others cannot. The procedure is to inoculate or streak the unknown bacteria into test tubes containing the biochemicals, or onto plates or tubes containing a gelled medium in which the biochemical is included. In most cases, particularly with the sugars and the amino acids, a test substance such as methyl red, bromthymal blue or the like would be included, these being substances which change in color with a given change in pH. Because of the relatively large number of test biochemicals which would normally be utilized for identification purposes (anywhere from about twelve to twenty-five or more, depending upon the nature of the symptoms caused, the location of the body from which the sample is taken, etc.), and due to the necessity that the inoculating needle or loop be flame-sterilized between each inoculation, a full program for a single species involving a typical number of biochemicals requires considerable time on the part of the laboratory technician.

After the various biochemicals have been inoculated in their separate test tubes and plates, these are then placed in an incubator or left to incubate at room temperature, in order to allow the bacterial sample to grow in the test medium if it is able to. If growth occurs, the indicator material will change color, and the lab technician is able to record the changes, and then by referring either to his own knowledge or to suitable reference texts, he attempts to establish a particular genus and species for the bacteria under examination. At this stage, human error can creep in. Confusion between the various sugar solutions or among the amino acid solutions occasionally takes place, and the result may be an incorrect identification, resulting in inappropriate treatment of the illness which may eithr prolong it or worsen the condition of the patient.

GENERAL DESCRIPTION OF THIS INVENTION

This invention seeks to shorten the time and reduce the risk of error involved in carrying out an identification program for a number of bacteriological samples. It utilizes apparatus capable of carrying out multiple inoculation, so that a plurality of samples can all be inoculated simultaneously onto a given culture medium. The method disclosed herein utilizes a computer-stored data-comparing capability in order to minimize the risk of human error.

Accordingly, this invention provides an apparatus for simultaneous multiple inoculation of bacterial samples located in a plurality of upwardly open pockets in a sample tray, the pockets being in a given geometric array, the apparatus comprising:

a plate-supporting member adapted for rotation in a horizontal plate about a vertical axis, and having a location spaced from said axis on which a culture plate may be positioned, first means for rotating the plate-supporting member through successive intervals, and allowing a dwell period between each interval of rotation, second means supporting an inoculation head above the plate-supporting member for vertical reciprocation at a location spaced from said vertical axis, the inoculation head having inoculation pins in the same geometric array as the said upwardly open pockets, third means for lodging the sample tray under the plane of rotation of the plate-supporting member and directly beneath the inoculation head with the pockets aligned with the inoculation pins, fourth means for controlling the vertical reciprocation of the inoculation head and the rotation of the plate-supporting member in a sequence of steps which include:
 (a) descent of the inoculation head to bring the pins into the open pockets of the sample tray to pick up bacteria therefrom,
 (b) raising of the inoculation head clear of the rotational path of the plate-supporting member,
 (c) rotation of the plate-supporting member to bring said location into alignment beneath the inoculation head,
 (d) descent of the inoculation head to bring the pins down into a culture plate at said location,
 (e) raising the inoculation head clear of the rotational path of the plate-supporting member, and
 (f) rotation of the plate-supporting member to remove said location from alignment beneath the inoculation head.

Further, this invention provides a method for the simultaneous multiple inoculation of bacterial samples located on a plurality of upwardly open pockets in a sample tray, the pockets being in a given geometric array, the method comprising the steps:

providing a plate-supporting member adapted for rotation in a horizontal plane about a vertical axis, and having a location spaced from said axis on which a culture plate may be positioned, positioning a culture plate at said location, at a location spaced from said vertical axis and above the plate-supporting member, supporting an inoculation head which has inoculation pins in the same geometric array as the said upwardly open pockets in the sample tray, lodging the sample tray under the plane of rotation of the plate-supporting member and directly beneath the inoculation head with the pockets aligned with the inoculation pins, causing the inoculation head to descend in order to bring the pins into the open pockets of the sample tray in order to pick up bacteria therefrom, raising the inoculation head clear of the rotational path of the plate-supporting member, rotating the plate-supporting member to bring the culture plate into alignment beneath the inoculation head, causing the inoculation head to descend again to bring the pins down into the culture plate, raising the inoculation head clear of the rotational path of the plate-supporting member, and removing the inoculated culture plate from alignment with the inoculation head.

Further, this invention provides a method for simultaneously identifying a plurality of bacterial samples, comprising the steps:

(a) culturing the samples on suitable nutrient in separate, upwardly open pockets in a sample tray, the pockets being in a given geometric array, (b) utilizing an inoculation head which has a plurality of inoculation pins in the same geometric array as the said pockets in the sample tray to pick up some of the culture in each pocket and then inoculating a culture plate with the pins, the culture plate being divided into separate compartments in the same geometric array as the pins, all compartments containing a given test substance to which bacterial sensitivity contributes to identification, along with a suitable indicator, (c) placing the culture plate in an environment which promotes growth of those bacteria not inhibited by the test substance, whereby growth is signalled by a color change in the indicator, (d) removing the culture plate from said environment and entering data identifying the compartments where growth has occurred into an electronic storage, (e) repeating steps (b), (c) and (d) with other test substances contained in additional culture plates, (f) using an electronic computing device to compare the sensitivity of the plurality of samples to the test substances with known reactions of known bacteria to the same test substances, thereby identifying the samples.

Further, this invention provides apparatus for simultaneously identifying a plurality of bacterial samples, comprising:

a sample tray with a plurality of upwardly open pockets in a given geometric array, a device which includes a reciprocating inoculation head having a plurality of inoculating pins in the same geometric array as the said pockets, whereby the pins can enter the pockets to pick up bacteria therefrom, and then can inoculate a plurality of culture plates, each compartmentalized in the same geometric array as the pins and each containing in all its compartments a test substance to which bacterial sensitivity contributes to identification, along with a suitable indicator, different plates containing different test substances, and a console for the entering of data identifying the compartments of each plate where growth has occurred, the console including an electronic storage, a location on which a culture plate can be positioned after incubation, a plurality of data-entering buttons, one for each compartment in a plate, the buttons being in the same geometric array as the compartments, and a computing facility adapted to compare the sensitivity of the plurality of samples to the test substances in the plates with known reactions of known bacteria to the same test substances, thereby identifying the samples.

GENERAL DESCRIPTION OF THE DRAWINGS

One embodiment of this invention is illustrated in the accompanying drawings, in which like numerals denote like parts throughout the several views, and in which:

FIG. 1 is a partly broken-away view of a multiple-inoculation apparatus constructed in accordance with this invention;

FIG. 2 is a view, from underneath, of one of the components of the apparatus shown in FIG. 1;

DETAILED DESCRIPTION OF THE DRAWINGS

Figure 3:
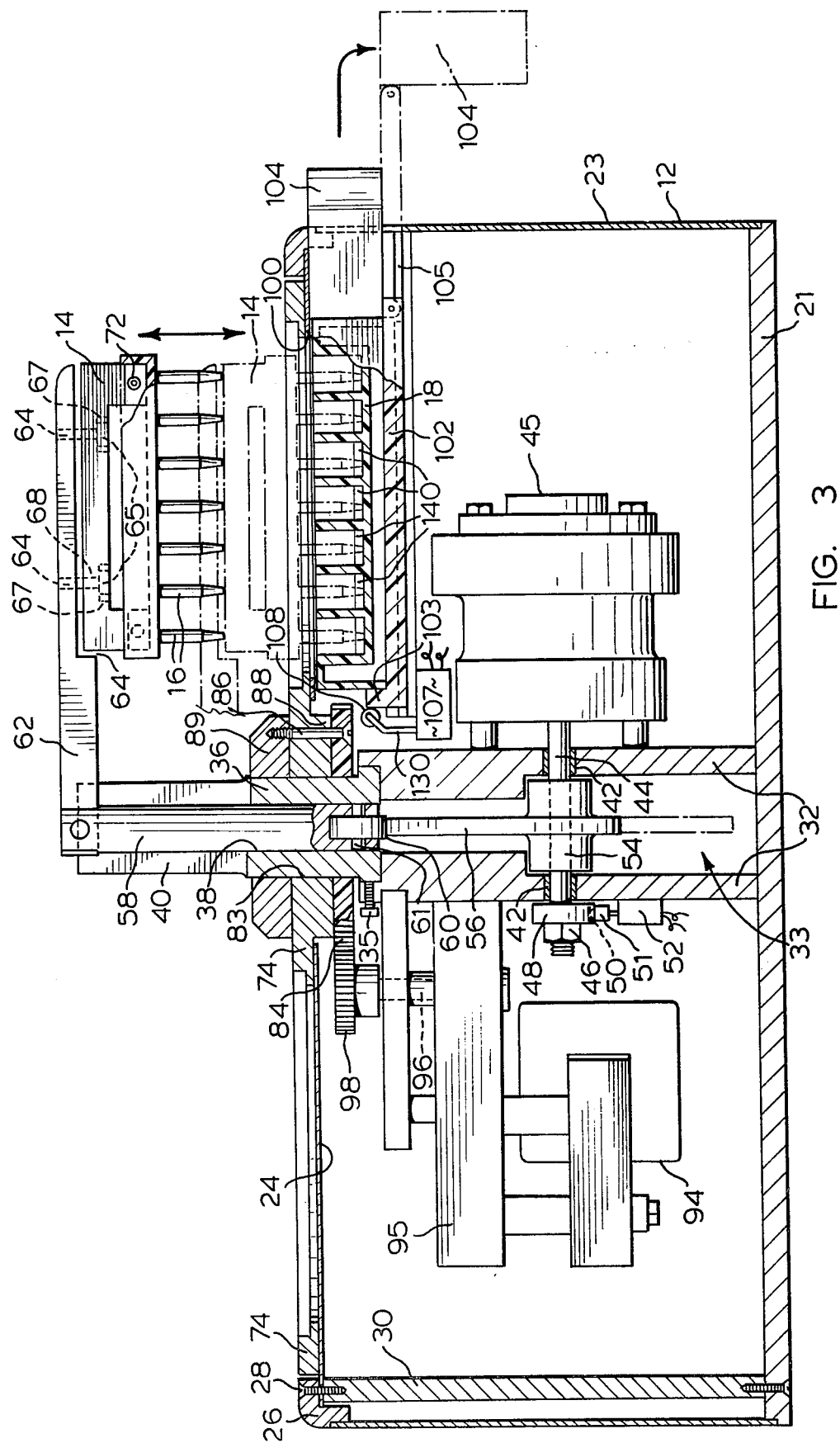
FIG. 3 is a sectional view taken along the lin 3—3 in FIG. 1.

Referring to FIG. 1, an apparatus for simultaneous multiple inoculation of bacterial samples is shown generally at the numeral 10. The apparatus includes a cylindrical base 12 and an inoculation head 14 located above and supported from the base 12. Means are provided for permitting vertical reciprocation of the inoculation head 14, and the latter is adapted to receive on its underside a cap 15 which defines a plurality of inoculation pins 16 projecting from the bottom. The pins 16 are positioned in a particular geometric array and are adapted to be inserted into a plurality of upwardly open pockets 17 of a sample tray 18 in order to pick up bacteria from the pockets 17, and then subsequently to be inserted into the compartments of a culture plate 20, both the pockets 17 and the compartments of the culture plate 20 being in the same geometric array as the pins 16. Insertion of the pins 16 into the compartments of the culture plate 20 will inoculate culture media within the compartments, so that the culture plate can then be incubated to grow bacterial colonies within the compartments.

The foregoing is a generalized description of the basic mode of operation of the apparatus shown in FIG. 1, and it is seen that this operational procedure accomplishes the simultaneous transfer of bacteria from a plurality of locations in one plate or tray to a plurality of locations in another plate, in a single action not requiring intermediate sterilization, complicated handling procedures, and the like. A detailed description of the apparatus now follows.

Referring to FIGS. 1 and 3, the cylindrical base 12 includes a circular bottom wall 21, a cylindrical side wall 23, and a circular top wall 24. A top edge moulding 26 joins together the adjacent margins of the top wall 24 and the side wall 23, and as can be seen at the left in FIG. 3, the bottom and top walls and the moulding 26 are held in place by being fastened with fasteners 28 to a plurality of vertical brace members 30, the latter being spaced at intervals around the circumference of the cylindrical base 12.

Turning now to FIG. 3, a central column member 32 is secured, by means not shown, to the centre of the bottom wall 21, and is upstanding therefrom. The column member is essentially cylindrical in its outer periphery, but is machined to define a central slot 33 which is wide at the lower end and more narrow at the upper end. At the upper end of the column member 32, a set screw 35 secures tightly into position a substantially cylindrical upstanding guide member 36, which has a central cylindrical bore 38 communicating with the upper end of the machined slot 33 of the column member 32, and which is itself slotted at 40 for a purpose which will be subsequently explained. The slot 40 is clearly seen in FIG. 1.

Returning to the column member 32, it will be seen in FIG. 3 that, toward the upper end of the wider portion of the slot, the walls of the column member 32 are provided with aligned bearings 42 in which is journaled the shaft 44 from a rotary power surface 45. In the preferred embodiment, the rotary power source 45 consists of an electric motor and a suitable speed-reduction mechanism, such that the shaft 44 is made to rotate at a speed in the region of 10 r.p.m.

Affixed to the leftward end of the shaft 44 by a locking nut 46 is a switch-tripping washer 48 which defines a recess 50 at one point of its periphery (located at the bottom in FIG. 3) into which the sensing member 51 of a microswitch 52 is adapted to lodge once for each complete cycle. Also secured to the shaft 44 is the boss 54 of a cam member 56, the function of which will be described shortly.

Figure 4:
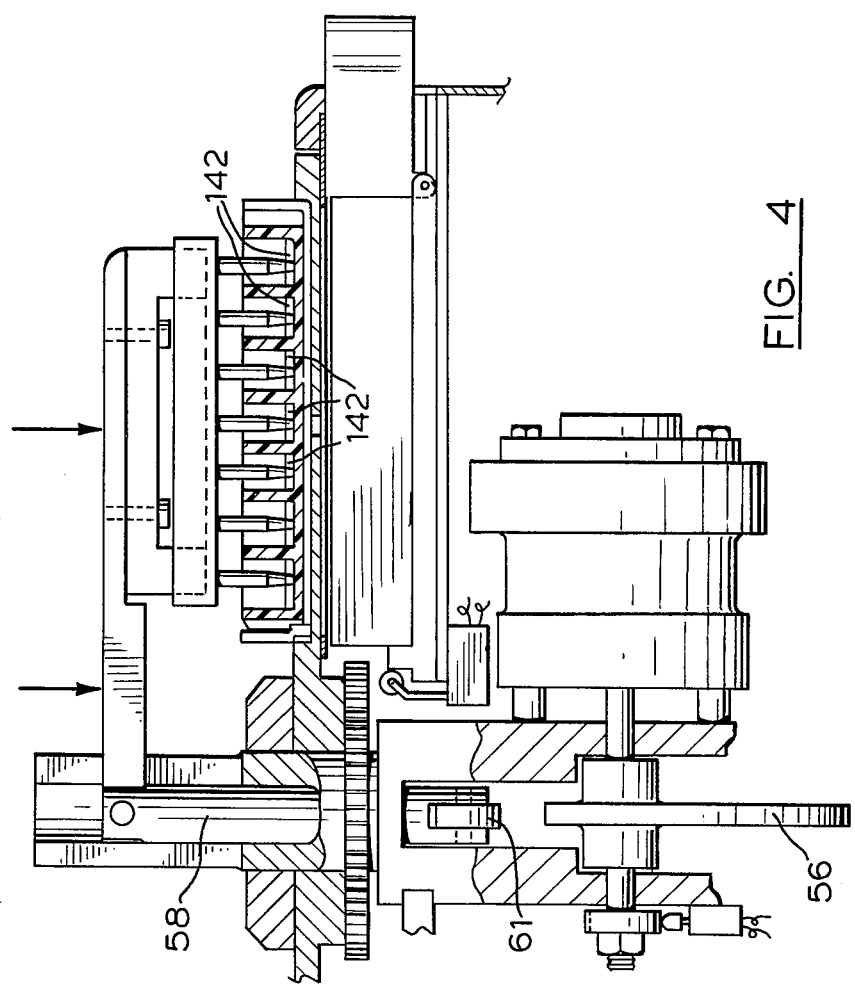
FIG. 4 is a partial view similar to FIG. 3, showing one of the components in a different state during the operation of the apparatus.

An elongated pin 58 is mounted for reciprocation within the bore 38 of the member 36. The pin 58 has, at its lower end, a cam follower wheel 60 freely rotating on a stub shaft 61 mounted transversely through the pin 58. The pin 58 is slotted to receive the cam follower wheel 60. At the upper end of the pin 58 is securely fastened the end of a transverse arm 62 which registers in the slot 40 as seen in FIGS. 1, 3 and 4, and which supports at its end remote from the pin 58 the inoculation head 14. The inoculation head 14 is supported from the arm 62 by two fastening members 64 which are secured rigidly to the arm 62 and which have heads 65 resting in enlarged pockets 67 in the inoculation head 14, the pockets 67 being defined at the bottom of oversized bores 68. The reason for the oversizing of the bores 68 and the pockets 67 is related to the desirability of allowing a certain adjustability of the inoculation head 14 with respect to the arm 62, whereby the inoculation head 14 has some freedom to move vertically and laterally with respect to the arm 62, and to tilt with respect to the arm 62. This allows the inoculation pins 16 to "find their own level" when they come down into the various media located in the sample tray 18 or the culture plate 20.

As seen in FIGS. 1 and 3, the cap 15 is in the shape of a rectangular tray having upstanding side walls 70 which are adapted to encompass the inoculation head 14, the latter being in the shape of an "H" as can been seen best in FIG. 1. The inoculation head 14 includes spring mounted snap-members 72, for example depressable ball-bearings urged outwardly by interior resilient members, which are intended to press against the inside face of one of the upstanding side walls 70 of the tray constituting the cap 15, whereby the cap 15 is retained in position on the inoculation head 14.

In FIG. 2 is shown a plate-supporting member 74 which is also visible in FIG. 1 as lying on top of the top wall 24 defined earlier with respect to FIG. 3. The plate-supporting member 74 is in the form of disc-like platter (which will be called platter 74 hereinafter) of which the details will now be described. The platter 74 is sized to fit closely but rotatably within the recess defined by the moulding 26 at the upper outer corner of the cylindrical base 12. Platter 74 also rests down upon the top wall 24, as best seen in FIG. 3.

As can be viewed in FIG. 2, the platter 74 defines two antipodally located circular openings 75 which are large enough to allow the pins 16 to pass through simultaneously. On its upper surface (seen in FIG. 1 but not seen in FIG. 2) there are defined two rectangular recesses 76 which concentrically surround the circular openings 75. The rectangular recesses 76 are sized to receive the cap 15, which is also rectangular. At the under marginal edge of the platter 74, aligned with the openings 75 are two diametrically opposed recesses 77, while at locations 90° spaced from the recesses 77 are larger, J-shaped recesses 79, which extend further inwardly toward the centre of the platter than do the recesses 77.

Located adjacent the J-shaped recesses 79, and still closer to the centre of the platter 74, are rectangular apertures 81. The purpose for these recesses and apertures will be described shortly.

The platter 74 defines a central opening 83 which is sized to snugly but rotatably surround the member 36, as can be seen in FIG. 3.

A ring gear 84 is mounted by fastening members 86 against the bottom of the platter 74 around the opening 83, the ring gear 84 having an opening of like diameter, which is in registry therewith. The platter 74 is thickened in the location surrounding the opening 83 to define a downwardly extending boss 88 against which the ring gear 84 is affixed. The fastener members 86 extend through the platter member 74 and threadedly engage a washer 89 which also has a central opening of the same diameter as the opening 83, and in registry therewith. There is thus defined an elongated composite opening of cylindrical configuration adapted snugly but rotatably to be received over the member 36, as shown in FIG. 3.

Lastly, the platter 74 defines on its upper surface, concentrically surrounding the small rectangular apertures 81, two plate-receiving circular recesses 91, seen in broken line in FIG. 2, but visible in the near and far location in solid lines in FIG. 1.

Each of these circular recesses 91 is interrupted at one location of its periphery by an inwardly projecting registration finger 92, the purpose of which will be explained subsequently.

A drive motor 94 is mounted within the cylindrical base 12 on suitable supports (nt identified), and its output is reduced in speed by a speed reducing mechanism 95 so that the output shaft 96 from the speed reducing mechanism 95 rotates at a relatively slow rate. Mounted on the output shaft 96 is a pinion gear 98 which engages the ring gear 84.

When the drive motor 94 is energized, the rotation of the pinion gear 98 causes the platter 74 to rotate at a speed in the region of 1 or 2 r.p.m.

As seen at the right in FIG. 3, the top wall 24 has a circular opening 100 which is seen in solid lines in the sectional view of FIG. 3, and is shown in broken line in FIG. 1. The opening 100 is slightly larger than the opening 75, and the centre of each opening 75 follows a locus which passes through the centre of the opening 100, such that these two openings can be brought into concentric registry.

Turning to FIG. 1, it will be seen at bottom right that the sample tray 18 is a solid rectangular block in which the pockets 17 have been drilled as cylindrical recesses. The particular geometric array shown in the drawings provides 37 pockets in the sample tray, the pockets being in 7 adjacent rows in a hexagonal overall outline, the rows in sequence having respectively: 4, 5, 6, 7, 6, 5 and 4 pockets. As pointed out above, the pins 16 and the compartments in the culture plate 20 would also have the same number of integers in the same geometric array. In order to permit the pins 16 to pick up bacteria from the pockets 17, the sample tray 18 must be lodged directly beneath the inoculation head, so that upon vertical reciprocation of the inoculation head 14 the pins 16 can enter the pockets 17. This lodging is accomplished by a tray holder 102 which has an upstanding ledge 103 at its inner end against which the sample tray 18 can abut, and which has a pivoted handle member 104 at its outer end positioned in such a manner that, when the handle member 104 is in its upward or locked position shown in solid lines in FIG. 3, the distance defined between the handle member 104 and the ledge 103 is the same as the corresponding dimension of the sample tray 18, whereby the latter is snugly held in position. When the handle member is rotated counter-clockwise as seen in FIG. 3 to the position shown in broken lines in FIG. 3, it is possible to withdraw the sample tray 18. The tray holder 102 is recessed at its side edges so as to receive and run along inwardly projecting track members 105 defined by appropriate portions of the internal structure of the cylindrical base 12.

A microswitch 107 is mounted toward the inner end of the tracks 105 and a sensing member 108 is adapted to be triggered when the tray holder 102 has reached the inner end of its movement. The function of the microswitch 107 will be explained subsequently.

Three further microswitches are provided in the apparatus herein disclosed, these being shown in FIG. 1 to which attention is now directed. A first microswitch 110 is mounted to the top wall 24 and has a sensing member 112 projecting upwardly through a suitable opening in the top wall 24 at that location, such that the sensing member 112 is aligned with the path of the rectangular apertures 81 in the platter 74, as the latter rotates. Thus, whenever one of the recesses 91 arrives at the condition in which the platter is shown in FIG. 1, the sensing member 112 is able to extend upwardly through the aperture 81 and would normally seek a position in which it extended somewhat above the plane of the bottom of the recess 91. When a culture plate 20 is positioned in the recess 91, however, the sensing member 112 of the microswitch 110 will be depressed. The microswitch is adjusted in such a way that it is in a first electronic condition when a culture plate recess 91 is positioned as shown in FIG. 1 without any culture plate thereof, and is in a second electronic condition under all other circumstances. Thus, the microswitch 110 is in the second electronic condition whenever the platter 74 is in a rotational position other than that shown in FIG. 1, and also when the platter 74 is in the condition of FIG. 1 but a culture plate is positioned in the recess 91 thereby depressing the sensing member 112.

Two other microswitches 114 and 115 are positioned in side-by-side relationship beneath the top wall 24 and secured thereto, at a location aligned radially with the microswitch 110 and adjacent the outer edge of the top wall 24. The sensing members 116 and 117 respectively are located such that the outermost sensing member 116 is adapted to lodge in the recesses 77 of the platter 74 shown in FIG. 2, and also in the recesses 79. The inner sensing member 117, however, is too far inwardly to register with the recesses 77, but does register in the enlarged portion of the J-shaped recesses 79.

Turning to the culture plate 20, it will be noted that it consists of a cylindrical base member 120 having a circular bottom wall 121 and a cylindrical side wall 122, together with a hexagonal, compartment-defining portion 124, which is divided by internal integral partitions into compartments 126 in the same geometric array as the pockets 17 of the sample tray 18. The hexagonal portion 124 also has an integral bottom wall which allows the compartments 126 to be completely isolated from one another.

Although the culture plate 20 consists only of the two portions shown for the purposes of the inoculation procedure utilizing the apparatus 10, when the same is being incubated subsequent to the inoculation in a standard incubator, it is understood that a cover plate would be placed over the two portions shown in FIG. 1, in order to prevent contamination of the medium from other sources, and to permit the usual inverted incubation position.

The sample tray 18 would also cooperate with a suitable cover member during its own period of incubation prior to the multiple inoculation procedure utilizing the apparatus 10.

The method by which the apparatus 10 is utilized for multiple inoculation will now be described.

It must first be understood that the initial step is to grow samples of the unknown bacteria in the various pockets 17 of the sample tray 18. As an example, it may be supposed that 37 suspected bacterial strains from different swabs, blood samples or the like are to be identified. It is assumed that the bacteria to be identified are uncontaminated with other strains. The process of isolating and separating one strain from another is well known in microbacteriological work, and forms no part of this invention. Once having obtained the particular bacterial strains to be identified, these are inoculated into the different pockets 17 of the sample tray 18, each pocket containing a suitable amount of a growth-supporting medium, for example blood agar, chocolate agar, or some other medium capable of supporting the growth of the majority of pathogenic bacteria. During the process of isolation for the initial bacterial samples, the laboratory technician will have determined which of the bacteria are strict anaerobes, and will ensure that the species inoculated into the pockets 17 of a given sample tray 18 are all either aerobic or anaerobic. This is necessary due to the different incubation conditions called for, the anaerobes requiring an atmosphere of $CO_2$.

Once the various samples have been inoculated into the pockets 17 of a sample tray 18, the same is incubated in the usual inverted condition in an incubator, either aerobically or anaerobically as required by the nature of the bacteria, in order to promote an abundant colony growth of the different species within each of the pockets 17.

After incubation, the technician inserts the sample tray 18 into the tray holder 102, closes the handle 104 into the uppermost position, and inserts the tray holder 102 into the cylindrical base 17 through the opening provided, with the tray holder 102 sliding along the guide rails 105. The technician shoves the tray holder 102 as far inwardly as it will go, until its inner end abuts a stop 130, and also contacts the sensing member 108 of the microswitch 107, throwing the latter from one electronic condition into another electronic condition.

The technician then places an incubation plate, containing a test medium which supports the growth of some bacteria and inhibits others in a known pattern, into the circular recess 91 which is located 90° clockwise from the inoculation head 14 as seen in FIG. 1. It is assumed here that, before initiating the operation of the apparatus 10, the platter is in the condition shown in FIG. 1, with one of the circular openings 75 in alignment with the opening 100, and directly beneath the inoculation head 14. This will mean that, prior to the depositing of the culture plate 20 within the recess 91, the sensing member 112 of the microswitch 110 projected upwardly through the aperture 81. The microswitch 110 thus senses the absence of a culture plate 20. When the technician places the culture plate into position in the recess 91, the microswitch 110 in effect "knows" that a culture plate is located in proper position for the operation of the apparatus.

The placing of the culture plate 20 in the proper position requires there to be registry between the finger 92 and a corresponding indentation at a location 131 on the lower outside margin of the cylindrical member 120, and also the hexagonal portion 124 must be received within the cylindrical portion 120 with two projecting fingers 134 in alignment with an inward projection 136 of the cylindrical portion 120. This will ensure that, when the platter 74 carries the culture plate 20 around to the location directly beneath the inoculation head 14, the various compartments 126 will be properly aligned with the pins 16.

Figure 5:
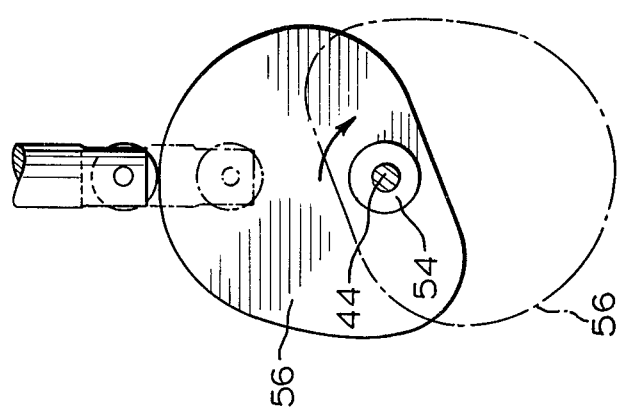
FIG. 5 is an elevational view of a cam element utilized in the apparatus shown in FIG. 4.

As soon as the culture plate 20 is deposited in the recess 91, the depression of the sensing member 112 of the microswitch 110 initiates a complete cycle of the apparatus 10. The first phase is the descent of the inoculation head 14 and the pins 16 into the pockets 17 of the sample tray 18. This is accomplished by energizing the rotary power source 45 which controls the position of the cam 56. Referring to FIG. 5, the cam 56 is in its upper or solid line position at the initiation and at the end of one complete cycle. During the clockwise rotation as seen in FIG. 5, the cam rotates through its lowermost position which allows the pin 58 to descend as far as the pins 16 will permit. When the apparatus 10 is in the condition shown in FIG. 1, there is nothing to prevent the pins 16 from descending all the way down into the pockets 17 and this is what occurs. The lowermost position for the inoculation head 14 and the pins 16 is shown in broken lines in FIG. 3. The pins 16 are seen projecting into the medium 140 in the bottom of each of the pockets 17. Thus, upon again rising to the uppermost position, the pins 16 will have picked up a portion of the bacterial cultures in each of the pockets 17, ready to be inoculated into the culture plate located in the nearer recess 19 in FIG. 1.

When the cam has rotated through one full revolution and has returned to the uppermost condition shown in solid lines in FIG. 5, the rotary power source 45 is stopped, and simultaneously the drive motor 94 is started. This carries the platter 74 around in the counter-clockwise direction as seen from above in FIG. 1, thus bringing the culture plate 91 around to a position directly beneath the inoculation head 14. The apparatus 10 knows when the culture plate has reached this alignment position because the sensing member 116 of the outermost microswitch 114 lodges in the leftward recess 77 as seen in FIG. 2, this recess having rotated around through 90° during the platter rotation just mentioned. (It is to be understood that both of the sensing members 116 and 117 project upwardly through suitable openings in the top wall 24, these not being seen in the Figures.)

As soon as the sensing member 116 lodges within the recess 77 of the platter 74, a signal is given which stops the drive motor 94 and again simultaneously initiates rotation of the power source 45, whereby the cam 56 undergoes another complete cycle returning to the top and stopping. During this cycle, the inoculation head 14 and the pins 16 again descend as far as they are able to, this time the descent being limited by the fact that the culture plate is located above the platter 74, i.e. at a level higher than the sample tray 18. However, since the pin 34 and the inoculation head 14 are in no way tied to the cam, no problem results. The cam profile simply drops down below the follower wheel 61 as can be seen in FIG. 4, and a short "dwell" period is encountered, while the cam profile and the follower wheel 61 are not in contact. This procedure inoculates the medium 142 in the bottoms of the compartments 126 with the bacterial species to be identified.

When the cam 56 again reaches the top of its cycle, the microswitch 52 senses that the cam cycle is completed, and simultaneously stops the rotary power source 45 and initiates rotation of the drive motor 94 in order to carry the platter 74 through a further 90° rotation. At the end of the 90° rotation, signalled by the arrival of one of the J-shaped recesses 79 at the microswitches 114 and 115 in FIG. 1, the drive motor 94 is stopped, and the apparatus 10 shuts down. The shutting down of the apparatus 10 is the function of the microswitch 117, which is activated only twice in each revolution of the platter 74, whereas the microswitch 116 is activated four times in each revolution.

Thus, after completion of the cycle, the platter is rotated through 180° from the condition shown in FIG. 1, but this position is really identical to that shown in FIG. 1, since all of the openings, recesses, etc. in the platter have a corresponding opening, recess, etc. at a location precisely 180° away. This is clear from an inspection of FIG. 2.

If the laboratory technician has, during the operation of the apparatus 10 through one complete cycle as just described, placed another culture plate in the other of the two recesses 91 of the platter 74, then upon completion of the first cycle the sensing member 112 will remain in a depressed condition due to the presence of the new culture plate, and a complete new cycle will be initiated. This will continue for as long as the technician supplies culture plates to the appropriate recess 91, either before the recess arrives at the microswitch 110 (in which case no pauses will be encountered), or after the appropriate recess 91 arrives at the microswitch 110 (in which case the platter 74 will halt at the position shown in FIG. 1 until the new plate is deposited in the recess 91).

So long as the platter 74 is not removed from the cylindrical base 12, the apparatus 10 will always shut down with the platter 74 in the position shown in FIG. 1, in which the sensing member 112 of the microswitch 110 registers with and projects upwardly through the aperture 81. However, it is sometimes necessary to remove the platter 74 for cleaning, adjustment, etc., and if this is necessary the procedure is firstly to lift out the pin 58 and the associated inoculation head 14, and then simply to lift the platter 74 upwardly off the member 36 about which it rotates. After cleaning or other required operation, the platter 74 is dropped down over the member 36, and when it comes down against the top wall 24, the ring gear 84 will again engage the pinion 98. However, it may happen that the operator does not drop the platter 74 down in a perfectly aligned position such that one of the apertures 81 registers precisely with the sensing member 112 of the microswitch 110. If this happens, then upon throwing the main switch of the apparatus 10, shown at the numeral 147 in FIG. 1, the fact of the sensing member 112 being depressed will call for rotation of the platter 74 by starting the drive motor 94, and the platter will thus rotate until both of the microswitches 110 and 117 register the presence of their respective aperture and recess, which can only take place when the platter 74 is in the position shown in FIG. 1 with one of the openings 75 of the platter member 74 directly beneath the inoculation head 14.

It is to be understood that each of the culture plates 20 which the operator would cause to be inoculated by the apparatus 10 would contain a different test medium which would also include an appropriate indicator, for example methyl red, capable of indicating a change in pH by a color change. When all of the required culture plates had been inoculated, they would be placed in an environment which promotes growth of those bacteria not inhibited by the test substance, so that where growth occurs this would be signalled by a color change in the indicator. Thus, each culture plate after incubation would typically show a pattern in which some compartments appeared one color and some another when viewed under illumination from the bottom. This would be the case unless all of the samples or none of the samples were able to grow on the particular medium.

Figure 6:
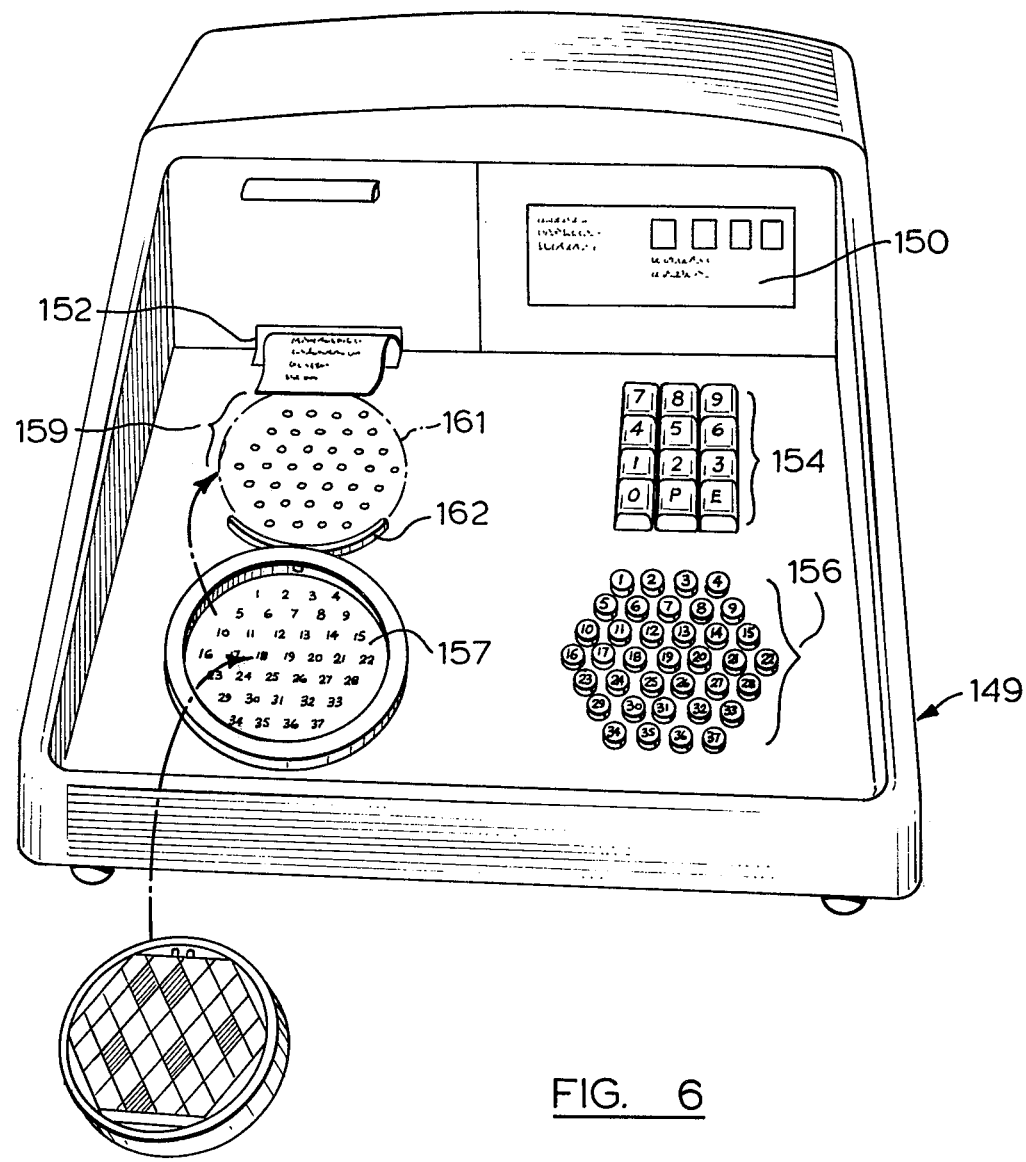
FIG. 6 is a perspective view of a console for the computer facility utilized in the method of this invention, showing features of the data-input section which minimize error and allow rapid entry of growth data for the bacteria.

Attention is now directed to FIG. 6, which illustrates a console 149 for a computing facility adapted to receive and store data relating to the particular bacterial samples which grew on the various test substances, and of comparing the pattern of growth on the test substances with stored data relating to known reactions of known bacteria to the same test substances.

The console 149 includes a digital readout portion 150, a print-out tape dispensing location 152, various entry buttons 154 by which the nature of the test substance in a given culture plate can be recorded, a hexagonal array of entry buttons 156 in exactly the same geometric array as the compartments 126 in each of the culture plates 120, and a recess 157 for receiving a culture plate, the recess 157 having a semi-transparent base and illumination means beneath the base to facilitate distinction between the plate compartments where growth occurs and those where no growth occurs. The console 149 also includes a plurality of light sources 159 in the same geometric array as the compartments, at a location directly adjacent the recess 157 and also close to the buttons 156. The light sources 159, which may be LED's, are wired to be switched on whenever the corresponding button in the group 156 of buttons is depressed.

The technician will enter into the console 149 information as to the compartments where growth occurred, by depressing only those buttons in the array 156 which correspond geometrically to the growth compartments in the culture plate. As the various buttons in the array 156 are depressed, the light sources in the grouping 159 will be illuminated, and this will allow the technician, after all of the data has been entered, visually to compare the geometric pattern of growth in a given culture plate while in the recess 157 with the lighted ones of the light sources in the grouping 159. As an additional check, the culture plate may be removed from the recess 157 and placed directly above the array of light sources 159 as seen in broken line at the numeral 161 in FIG. 6. An arcuate member 162 may be provided, against which the culture plate can lodge for this additional check procedure.

After all the data has been entered, the technician instructs the computer to compare the sensitivity pattern of the unknown bacteria to known patterns of known species, and to print its results in the form of the known species most closely corresponding to the sensitivity pattern of each of the bacteria being tested.

We claim:

1. Apparatus for simultaneous multiple inoculation of bacterial samples located in a plurality of upwardly open pockets in a sample tray, the pockets being in a given geometric array, the apparatus comprising:
   a plate-supporting member adapted for rotation in a horizontal plane about a vertical axis, and having a location spaced from said axis on which a culture plate may be positioned,
   first means for rotating the plate-supporting member through successive intervals, and allowing a dwell period between each interval of rotation,
   second means supporting an inoculation head above the plate-supporting member for vertical reciprocation at a location spaced from said vertical axis, the inoculation head having inoculation pins in the same geometric array as the said upwardly open pockets,
   third means for lodging the sample tray under the plane of rotation of the plate-supporting member and directly beneath the inoculation head with the pockets aligned with the inoculation pins,
   fourth means for controlling the vertical reciprocation of the inoculation head and the rotation of the plate-supporting member in a sequence of steps which include:
   (a) descent of the inoculation head to bring the pins into the open pockets of the sample tray to pick up bacteria therefrom,
   (b) raising of the inoculation head clear of the rotational path of the plate-supporting member,
   (c) rotation of the plate-supporting member to bring said location into alignment beneath the inoculation head,
   (d) descent of the inoculation head to bring the pins down into a culture plate at said location,
   (e) raising the inoculation head clear of the rotational path of the plate-supporting member, and
   (f) rotation of the plate-supporting member to remove said location from alignment beneath the inoculation head.

2. The apparatus claimed in claim 1, in which the plate-supporting member is a disc-like platter having age, location on which a culture plate can be positioned after incubation, a plurality of data-entering buttons, one for each compartment in a plate, the buttons being in the same geometric array as the compartments, and a computing facility adapted to compare the sensitivity of the plurality of samples to the test substances in the plates with known reactions of known bacteria to the same test substances, thereby identifying the samples.

11. The apparatus claimed in claim 10, in which the said location is illuminated from within the console such that a plate placed thereon is lit from beneath, and in which the console further includes a plurality of light sources in the same geometric array as the compartments at a location close to the said buttons, the light sources being wired to be switched on whenever the positionally corresponding button is depressed, whereby the operator, after entering all the data regarding a given plate, can visually compare the pattern of light sources with the plate to ensure that no error has occurred.

12. The apparatus claimed in claim 10, in which the said device further includes a culture plate-supporting member adapted for rotation in a horizontal plane about a vertical axis, and having a plate location spaced from said axis on which a culture plate may be positioned, first means for rotating the culture plate-supporting member through successive intervals, and allowing a dwell period between each interval of rotation, second means supporting the said inoculation head above the culture plate-supporting member for vertical reciprocation at a location spaced from said vertical axis, third means for lodging the sample tray under the plane of rotation of the culture plate-supporting member and directly beneath the inoculation head with the pockets aligned with the inoculation pins, and fourth means for controlling the vertical reciprocation of the inoculation head and the rotation of the plate-supporting member in a sequence of steps which include:

(a) descent of the inoculation head to bring the pins into the open pockets of the sample tray to pick up bacteria therefrom, (b) raising of the inoculation head clear of the rotational path of the plate-supporting member, (c) rotation of the plate-supporting member to bring said plate location into alignment beneath the inoculation head, (d) descent of the inoculation head to bring the pins down into a culture plate at said location, (e) raising the inoculation head clear of the rotational path of the plate-supporting member, and (f) rotation of the plate-supporting member to remove said plate location from alignment beneath the inoculation head.

13. The apparatus claimed in claim 12, in which the plate-supporting member is a disc-like platter having two eccentric openings equally spaced from the axis and diametrically opposed to each other, said openings being positioned to pass directly under the inoculation head upon rotation of the platter, whereby the inoculation head can descend through one of the openings to bring the pins into the open pockets of the sample tray, the platter also defining two culture plate locations at 90° intervals from said openings.

14. The apparatus claimed in claim 12, in which said first means includes a drive motor, a speed reduction mechanism with an input from said drive motor and an output shaft with a lower rotational speed than the motor speed, a pinion gear mounted on the output shaft, and a ring gear mounted to the underside of the platter concentric with said vertical axis and engaging said pinion gear.

15. The apparatus claimed in claim 14, in which the fourth means includes first platter-sensing means mounted in a stationary location adjacent the platter, the platter having first activating means at 90° intervals on a locus aligned with the platter-sensing means whereby the platter-sensing means is activated once for each 90° interval of rotation, the activating means and the platter sensing means being located such that in two of the positions in which the platter-sensing means is activated one of the said eccentric openings is located directly under the said inoculation head; and in which the second means includes a vertically reciprocable shaft aligned concentrically with the vertical axis and supporting the inoculation head such that the shaft and the head reciprocate together, a cam rotatable about a horizontal axis and located under the shaft, the cam being contoured to cause the shaft to reciprocate as the cam rotates drive means for the cam, and cam-sensing means associated with the drive means for providing a signal after movement of the cam sufficient to fully lower and fully raise the shaft.

16. The apparatus claimed in claim 15, in which the fourth means further includes second platter-sensing means adjacent the platter, the platter having second activating means at 180° intervals on a locus aligned with the second platter-sensing means, whereby the second platter-sensing means is activated whenever the platter arrives at a position in which one of the eccentric openings is located under the inoculation head, a plate-sensing means located adjacent the platter and adapted to be in a first condition electronically when a culture plate location without any culture plate thereon is positioned such that it is located 90° back from being directly under the inoculaton head, and to be in a second condition electronically under all other circumstances; the fourth means also including electronic logic for carrying out the following functions:

(a) upon supply of electrical power to the apparatus, sensing the condition of said second platter-sensing means and if the same is in an unactivated condition, starting said drive motor to rotate the platter until the second platter-sensing means becomes activated;

(b) shutting off the drive motor upon activation of the second platter-sensing means, simultaneously detecting the condition of the plate-sensing means, and if the plate-sensing means is in said second condition due to the presence of a culture plate, re-starting the drive motor;

(c) detecting when the first platter-sensing means goes to an activated condition after 90° of rotation from said re-starting of the drive motor, and upon such detection shutting off the drive motor and simultaneously starting the cam motor;

(d) detecting a signal from the cam-sensing means after a completed down-up reciprocation cycle of the shaft and the inoculation head, and upon such detection halting the cam motor and re-starting the drive motor;

(e) again detecting when the first platter-sensing means goes to an activated condition after 90° furtwo eccentric openings equally spaced from the axis and diametrically opposed to each other, said openings being positioned to pass directly under the inoculation head upon rotation of the platter, whereby the inoculation head can descend through one of the openings to bring the pins into the open pockets of the sample tray, the platter also defining two culture plate locations at 90° intervals from said openings.

3. The apparatus claimed in claim 2, in which said first means includes a drive motor, a speed reduction mechanism with an input from said drive motor and an output shaft with a lower rotational speed than the motor speed, a pinion gear mounted on the output shaft, and a ring gear mounted to the underside of the platter concentric with said vertical axis and engaging said pinion gear.

4. The apparatus claimed in claim 2 or claim 3, in which the fourth means includes first platter-sensing means mounted in a stationary location adjacent the platter, the platter having first activating means at 90° intervals on a locus aligned with the platter-sensing means whereby the platter-sensing means is activated once for each 90° interval of rotation, the activating means and the platter-sensing means being located such that in two of the positions in which the platter-sensing means is activated one of the said eccentric openings is located directly under the said inoculation head.

5. The apparatus claimed in claim 3, in which the fourth means includes first platter-sensing means mounted in a stationary location adjacent the platter, the platter having first activating means at 90° intervals on a locus aligned with the platter-sensing means whereby the platter-sensing means is activated once for each 90° interval of rotation, the activating means and the platter sensing means being located such that in two of the positions in which the platter-sensing means is activated one of the said eccentric openings is located directly under the said inoculation head; and in which the second means includes a vertically reciprocable shaft aligned concentrically with the said vertical axis and supporting the inoculation head such that the shaft and the head reciprocate together, a cam rotatable about a horizontal axis and located under the shaft, the cam being contoured to cause the shaft to reciprocate as the cam rotates, drive means for the cam, and cam-sensing means associated with the drive means for providing a signal after movement of the cam sufficient to fully lower and fully raise the shaft.

6. The apparatus claimed in claim 5, in which the fourth means further includes second platter-sensing means adjacent the platter, the platter having second activating means at 180° intervals on a locus aligned with the second platter-sensing means, whereby the second platter-sensing means is activated whenever the platter arrives at a position in which one of the eccentric openings is located under the inoculation head, a plate-sensing means located adjacent the platter and adapted to be in a first condition electronically when a culture plate location without any culture plate thereon is positioned such that it is located 90° back from being directly under the inoculation head, and to be in a second condition electronically under all other circumstances; the fourth means also including electronic logic for carrying out the following functions:

(a) upon supply of electrical power to the apparatus, sensing the condition of said second platter-sensing means and if the same is in an unactivated condition, starting said drive motor to rotate the platter until the second platter-sensing means becomes activated;

(b) shutting off the drive motor upon activation of the second platter-sensing means, simultaneously detecting the condition of the plate-sensing means, and if the plate-sensing means is in said second condition due to the presence of a culture plate, re-starting the drive motor;

(c) detecting when the first platter-sensing means goes to an activated condition after 90° of rotation from said re-starting of the drive motor, and upon such detection shutting off the drive motor and simultaneously starting the cam motor;

(d) detecting a signal from the cam-sensing means after a completed down-up reciprocation cycle of the shaft and the inoculation head, and upon such detecting halting the cam motor and re-starting the drive motor;

(e) again detecting when the first platter-sensing means goes to an activated condition after 90° further platter rotation, and upon such detection halting the drive motor and re-starting the cam motor;

(f) again detecting a signal from the cam-sensing means after a further completed down-up reciprocation cycle of the shaft and the inoculation head, and upon such detection halting the cam motor and re-starting the drive motor;

(g) and again detecting when the first platter-sensing means goes to an activated condition after 90° further platter rotation, and upon such detection shutting off the drive motor.

7. The apparatus claimed in claim 6, in which both platter-sensing means and the cam-sensing means are microswitches.

8. The apparatus claimed in claim 1, in which the second means includes a vertically reciprocable shaft aligned concentrically with the said vertical axis and supporting the inoculation head such that the shaft and the head reciprocate together, a cam rotatable about a horizontal axis and located under the shaft, the cam being contoured to cause the shaft to reciprocate as the cam rotates, drive means for the cam, and cam-sensing means associated with the drive means for providing a signal after movement of the cam sufficient to fully lower and fully raise the shaft.

9. The apparatus claimed in claim 1, in which the said geometric array provides 37 pockets in the sample tray, the pockets being in seven adjacent rows in a hexagonal overall outline, the rows in sequence having respectively 4, 5, 6, 7, 6, 5 and 4 pockets.

10. Apparatus for simultaneously identifying a plurality of bacterial samples, comprising:

a sample tray with a plurality of upwardly open pockets in a given geometric array, a device which includes a reciprocating inoculation head having a plurality of inoculating pins in the same geometric array as the said pockets, whereby the pins can enter the pockets to pick up bacteria therefrom, and then can inoculate a plurality of culture plates, each compartmentalized in the same geometric array as the pins and each containing in all its compartments a test substance to which bacterial sensitivity contributes to identification, along with a suitable indicator, different plates containing different test substances, and a console for the entering of data identifying the compartments of each plate where growth has occurred, the console including an electronic storther platter rotation, and upon such detection halting the drive motor and re-starting the cam motor;
(f) again detecting a signal from the cam-sensing means after a further completed down-up reciprocation cycle of the shaft and the inoculation head, and upon such detection halting the cam motor and re-starting the drive motor;
(g) and again detecting when the first platter-sensing means goes to an activated condition after 90° further platter rotation, and upon such detection shutting off the drive motor.

17. The apparatus claimed in claim 16, in which both platter-sensing means and the cam-sensing means are micro-switches.

18. The apparatus claimed in claim 13 or claim 14, in which the fourth means includes first platter-sensing means mounted in a stationary location adjacent the platter, the platter having first activating means at 90° intervals on a locus aligned with the platter-sensing means whereby the platter-sensing means is activated once for each 90° interval of rotation, the activating means and the platter-sensing means being located such that in two of the positions in which the platter-sensing means is activated one of the said eccentric openings is located directly under the said inoculation head.

19. The apparatus claimed in claim 12, in which the second means includes a vertically reciprocable shaft aligned concentrically with the said vertical axis and supporting the inoculation head such that the shaft and the head reciprocate together, a cam rotatable about a horizontal axis and located under the shaft, the cam being contoured to cause the shaft to reciprocate as the cam rotates, drive means for the cam, and cam-sensing means associated with the drive means for providing a signal after movement of the cam sufficient to fully lower and fully raise the shaft.

20. The apparatus claimed in claim 12, in which the said geometric array provides 37 pockets in the sample tray, the pockets being in seven adjacent rows in a hexagonal overall outline, the rows in sequence having respectively 4, 5, 6, 7, 6, 5, and 4 pockets.

21. A method for simultaneously identifying a plurality of bacterial samples, comprising the steps
(a) culturing the samples on suitable nutrient in separate, upwardly open pockets in a sample tray, the pockets being in a given geometric array,
(b) utilizing an inoculation head which has a plurality of inoculation pins in the same geometric array as the said pockets in the same tray to pick up some of the culture in each pocket and then inoculating a culture plate with the pins, the culture plate being divided into separate compartments in the same geometric array as the pins, all compartments containing a given test substance to which bacterial sensitivity contributes to identification, along with a suitable indicator,
(c) placing the culture plate in an environment which promotes growth of those bacteria not inhibited by the test substance, whereby growth is signalled by a color change in the indicator,
(d) removing the culture plate from said environment and entering data identifying the compartments where growth has occurred into an electronic storage,
(e) repeating steps (b), (c) and (d) with other test substances contained in additional culture plates,
(f) using an electronic computing device to compare the sensitivity of the plurality of samples to the test substances with known reactions of known bacteria to the same test substances, thereby identifying the samples,
there being provided a plurality of light sources in the same geometric array as the compartments at a location close to the said buttons, the light sources being wired to be switched on whenever the corresponding button is depressed, whereby the operator, after entering all the data regarding a given plate, can visually compare the pattern of light sources with the plate to ensure that no error has occurred.

22. The method claimed in claim 21, which includes illuminating the plate from underneath, to aid visual distinction between the compartments where growth has occured and those where it has not.

* * * * *